United States Patent
Wirtz et al.

(10) Patent No.: US 9,668,670 B2
(45) Date of Patent: Jun. 6, 2017

(54) ENDORECTAL PROSTATE COIL WITH OPEN ACCESS FOR SURGICAL INSTRUMENTS

(71) Applicant: KONINKLIJKE PHILIPS N.V., Eindhoven (NL)

(72) Inventors: Daniel Wirtz, Hamburg (DE); Peter Mazurkewitz, Hamburg (DE); Christoph Leussler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 26 days.

(21) Appl. No.: 14/419,620

(22) PCT Filed: Aug. 5, 2013

(86) PCT No.: PCT/IB2013/056400
§ 371 (c)(1),
(2) Date: Feb. 4, 2015

(87) PCT Pub. No.: WO2014/024112
PCT Pub. Date: Feb. 13, 2014

(65) Prior Publication Data
US 2015/0208944 A1    Jul. 30, 2015

Related U.S. Application Data

(60) Provisional application No. 61/680,835, filed on Aug. 8, 2012.

(51) Int. Cl.
*G01R 33/28* (2006.01)
*A61B 5/055* (2006.01)
(Continued)

(52) U.S. Cl.
CPC .............. *A61B 5/055* (2013.01); *A61B 10/02* (2013.01); *A61B 17/0218* (2013.01);
(Continued)

(58) Field of Classification Search
CPC .................................. G01R 33/28; A61B 5/05
See application file for complete search history.

(56) References Cited

U.S. PATENT DOCUMENTS

| 5,170,789 A | 12/1992 | Narayan |
| 5,365,928 A | 11/1994 | Rhinehart |
| 5,451,232 A | 9/1995 | Rhinehart et al. |

(Continued)

FOREIGN PATENT DOCUMENTS

| EP | 0841575 A1 | 5/1998 |
| WO | 2012003211 A1 | 1/2012 |

OTHER PUBLICATIONS

"MR-Visible Coatings for Endovascular Device Visualization" by O. Unal et al. J Mag Res Imag 23:763-769 (2006).*

*Primary Examiner* — Tse Chen
*Assistant Examiner* — Jason Ip

(57) ABSTRACT

An endorectal coil (1) includes a tube (40), a spreader (44), and one or more electrically conductive elements (64). The tube (40) is configured for insertion into the rectum (42). The spreader (44) is configured to be positioned at a distal end of the tube (40) and mechanically spread to compress surrounding tissue after the tube (40) is inserted. The one or more electrically conductive elements (64) are tuned to receive magnetic resonance data disposed on at least one of the tube (40), the spreader (44), and adjacent the tube and spreader.

4 Claims, 11 Drawing Sheets

(51) Int. Cl.
*A61B 10/02* (2006.01)
*A61B 17/02* (2006.01)
*A61B 18/00* (2006.01)
*G01R 33/34* (2006.01)

(52) U.S. Cl.
CPC ............ A61B 18/00 (2013.01); G01R 33/286 (2013.01); G01R 33/34084 (2013.01); *A61B 2018/005* (2013.01); *A61B 2018/00577* (2013.01); *A61B 2018/00982* (2013.01); *G01R 33/285* (2013.01); *G01R 33/34046* (2013.01); *G01R 33/34069* (2013.01)

(56) References Cited

U.S. PATENT DOCUMENTS

| | | | | |
|---|---|---|---|---|
| 5,699,801 | A * | 12/1997 | Atalar | A61B 5/055 324/318 |
| 6,950,063 | B2 * | 9/2005 | Nesteruk | G01R 33/285 342/423 |
| 7,747,310 | B2 | 6/2010 | Misic | |
| 8,989,841 | B2 | 3/2015 | Misic | |
| 2001/0002445 | A1 * | 5/2001 | Vesely | A61F 2/2409 623/2.11 |
| 2003/0187347 | A1 * | 10/2003 | Nevo | A61B 5/06 600/424 |
| 2004/0046557 | A1 | 3/2004 | Karmarkar | |
| 2007/0135803 | A1 * | 6/2007 | Belson | A61B 1/00154 606/1 |
| 2008/0157772 | A1 * | 7/2008 | Okamoto | G01R 33/3415 324/322 |
| 2009/0082664 | A1 | 3/2009 | Schilling | |
| 2011/0215807 | A1 | 9/2011 | Misic | |

* cited by examiner

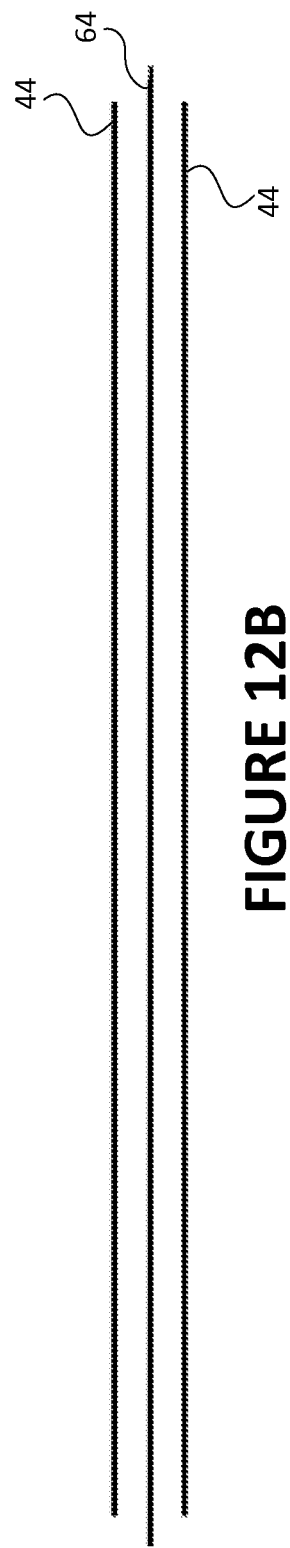

ENDORECTAL PROSTATE COIL WITH OPEN ACCESS FOR SURGICAL INSTRUMENTS

CROSS-REFERENCE TO PRIOR APPLICATIONS

This application is the U.S. National Phase application under 35 U.S.C. §371 of International Application No. PCT/IB2013/056400, filed on Aug. 5, 2013, which claims the benefit of U.S. Provisional Patent Application No. 61/680,835, filed on Aug. 8, 2012. These applications are hereby incorporated by reference herein.

The following relates generally to medical imaging. It finds particular application in conjunction with magnetic resonance local imaging coils, and will be described with particular reference thereto. However, it will be understood that it also finds application in other usage scenarios and is not necessarily limited to the aforementioned application.

Magnetic resonance (MR) imaging provides detailed anatomical and metabolic information of a subject. MR imaging involves no ionizing radiation and works by exciting magnetic resonance in tissue of the subject. Magnetic resonance occurs within a static main field $B_0$ which is typically oriented horizontal or vertical. Radio frequency (RF) pulses are applied to excite resonance. Gradient fields are applied across the static field to focus and manipulate resonance in the subject. The local coils receive the weak magnetic resonance decay RF signals close to the body and retransmit the received signals to a receiver. The magnetic field direction of the received RF field is orthogonal to the magnetic field direction of the main field ($B_0$). The received RF data is reconstructed into one or more images.

One common region of interest is the prostate region to image cancer tissue. Currently, MR scanners with horizontal main fields typically use a dedicated abdominal coil to excite resonance in the prostate tissue of the subject. Typically, abdominal coils enclose the lower torso, but do not obstruct the groin area. The lack of obstruction of the groin area is advantageous because biopsies can be taken with a biopsy device inserted in the rectum. Although, MR scanners with horizontal main fields can image and position the biopsy device, typically healthcare practitioners use transrectal ultrasound (TRUS) to guide the biopsies. A bore of a horizontal main field MR scanner is toroidal in shape and includes an enclosed area in which the subject is placed for imaging and limits the freedom of movement of the subject. Although the MR is preferable to TRUS for anatomical and metabolic information, TRUS is not restricted by the enclosed bore opening.

The prostate is a walnut sized gland located just in front of the rectum. The prostate is located between the bladder and the penis. A biopsy can determine cancerous tissue with a sampling of the prostate tissue taken by needle biopsies. Needles penetrate through the wall of the rectum and into the prostate and typically take a column of tissue as a biopsy sample. Samples are taken of various portions of the prostate. Positioning of the needle is important to take the appropriate samples. TRUS guides the spatial positioning of the needle for the biopsy, but without the anatomical and metabolic detail. Access to take a biopsy is typically through the rectum because the prostate is located just in front of the rectum. Access from other directions would involve other anatomical structures such as the bladder which is undesirable. Typically, the patient lies with knees bent to provide access to the rectum.

MR scanners with vertical main fields such as c-type or open system magnet configurations remove the enclosed bore constraint of horizontal field MR scanners and provide a more open access to the subject during imaging. However with the reorientation of the static main field, dedicated abdominal coils designed for horizontal main fields do not operate effectively for horizontal subjects. In a horizontal main field, the static main field is parallel to the axis of the subject. In a vertical main field, the static main field is perpendicular to the axis of the subject.

The following discloses a new and improved endorectal prostate coil which addresses the above referenced issues, and others.

In accordance with one aspect, an endorectal coil includes a tube, a spreader, and one or more electrically conductive elements. The tube is configured for insertion into a rectum. The spreader is configured to be positioned at a distal end of the tube and mechanically spread to compress surrounding tissue after the tube is inserted. The one or more electrically conductive elements are tuned to receive magnetic resonance data disposed on at least one of the tube, the spreader, and adjacent the tube and spreader.

In accordance with another aspect, method of imaging with an endorectal coil includes inserting a tube through the rectum. A spreader positioned at the end of the tube is mechanically spread to compress surrounding tissue. Magnetic resonance data are acquired with one or more electrically conductive elements disposed on at least one of the spreader, the tube, and adjacent the tube or the spreader. The magnetic resonance data is reconstructed into images.

In accordance with another aspect, An endorectal prostate coil includes a tube and one or more electrically conductive elements. The tube is insertable through a rectum. The one or more electrically conductive elements are disposed on the tube and tuned to receive magnetic resonance data and form one of saddle coils configured to receive MR data in quadrature in a horizontal main field, and conductive loops wrapped in a slanted, criss-cross pattern around the tube and cross perpendicular to each other and configured to receive MR data in quadrature in a vertical main field.

One advantage is the use and operation of a local prostate or abdominal coil with a vertical main field magnetic resonance system.

Another advantage resides in open access for surgical instruments to take biopsies.

Another advantage resides in a local imaging coil for detailed and metabolic imaging of the prostate region while taking the biopsy.

Another advantage resides in the ability of a spreader to flatten the prostate during imaging and taking of biopsies.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 diagrammatically illustrates one embodiment of the endorectal prostate coil within a magnetic resonance system.

FIG. 2 diagrammatically illustrates one embodiment of the endorectal prostate coil with a deployed surgical instrument.

Figure 5:
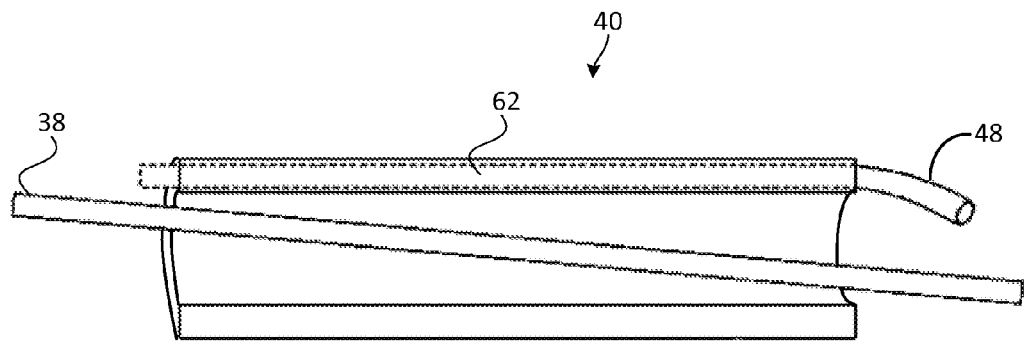

FIG. 5 diagrammatically illustrates an embodiment of a coil tube with a deployed surgical instrument.

Figure 6:
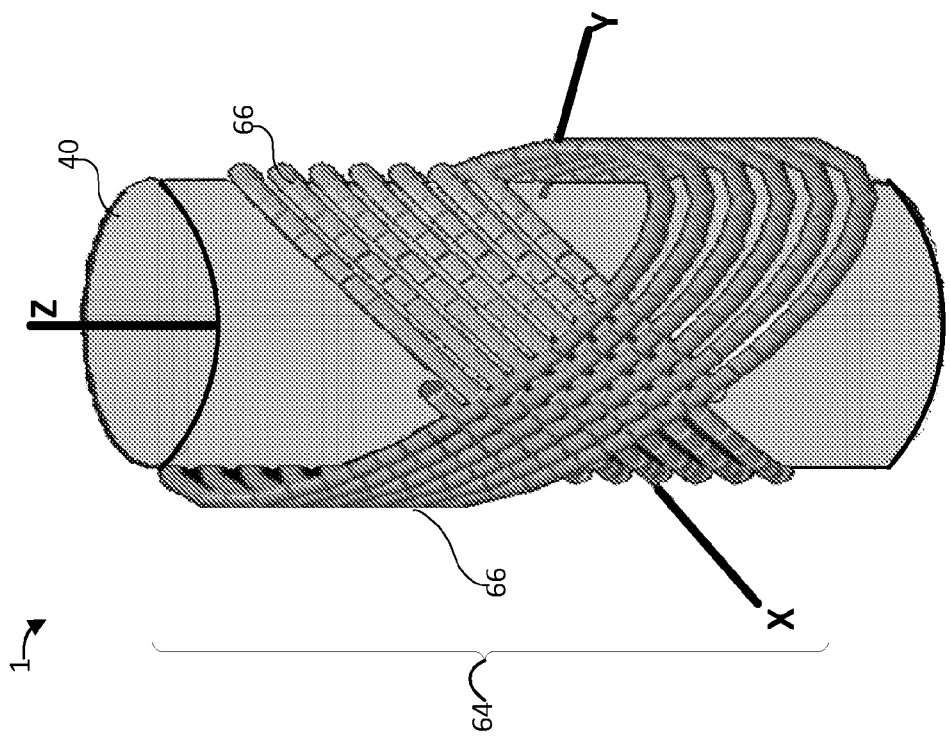

FIG. 6 diagrammatically illustrates one embodiment of the local prostate coil with coil elements located on the guide tube.

Figure 7:
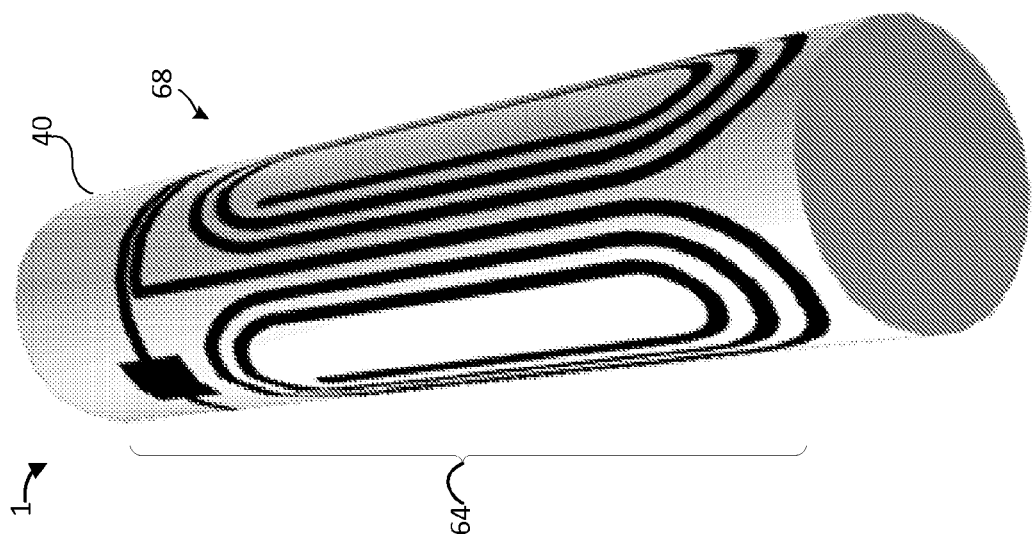

FIG. 7 diagrammatically illustrations another embodiment of the local prostate coil with coil elements located on the guide tube.

Figure 8:
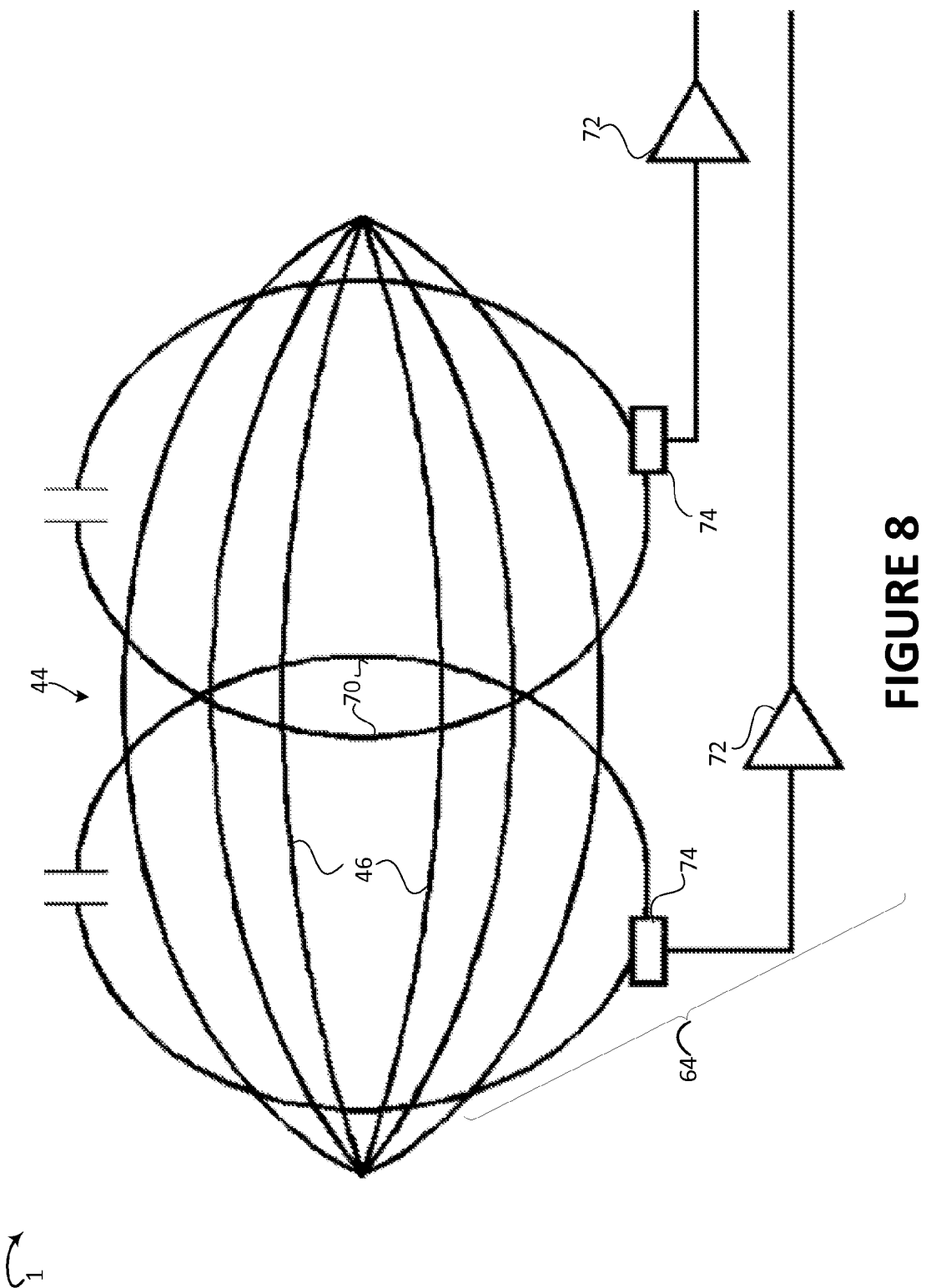

FIG. 8 diagrammatically illustrates one embodiment of the local prostate coil with coil elements located on the spreader.

Figure 9:
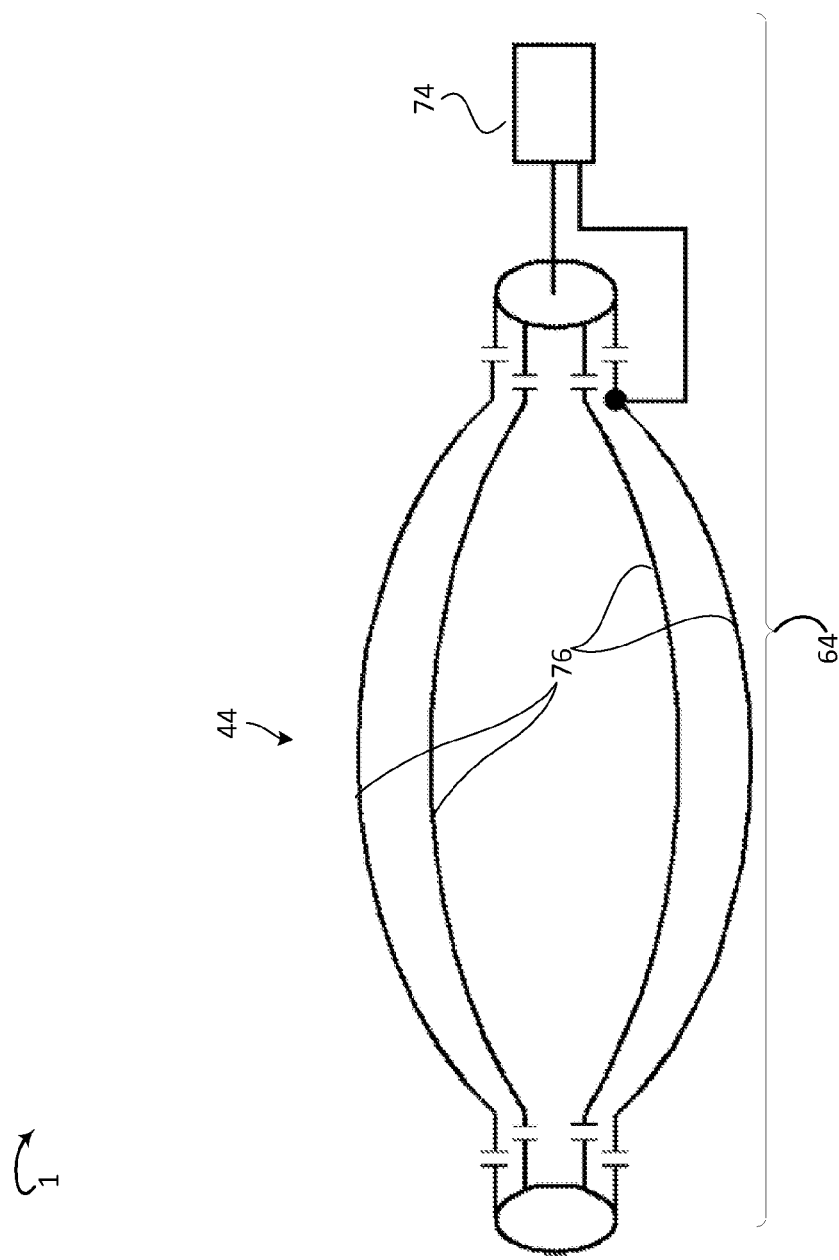

FIG. 9 diagrammatically illustrates another embodiment of the local prostate coil with coil elements integrated with the spreader.

Figure 10:
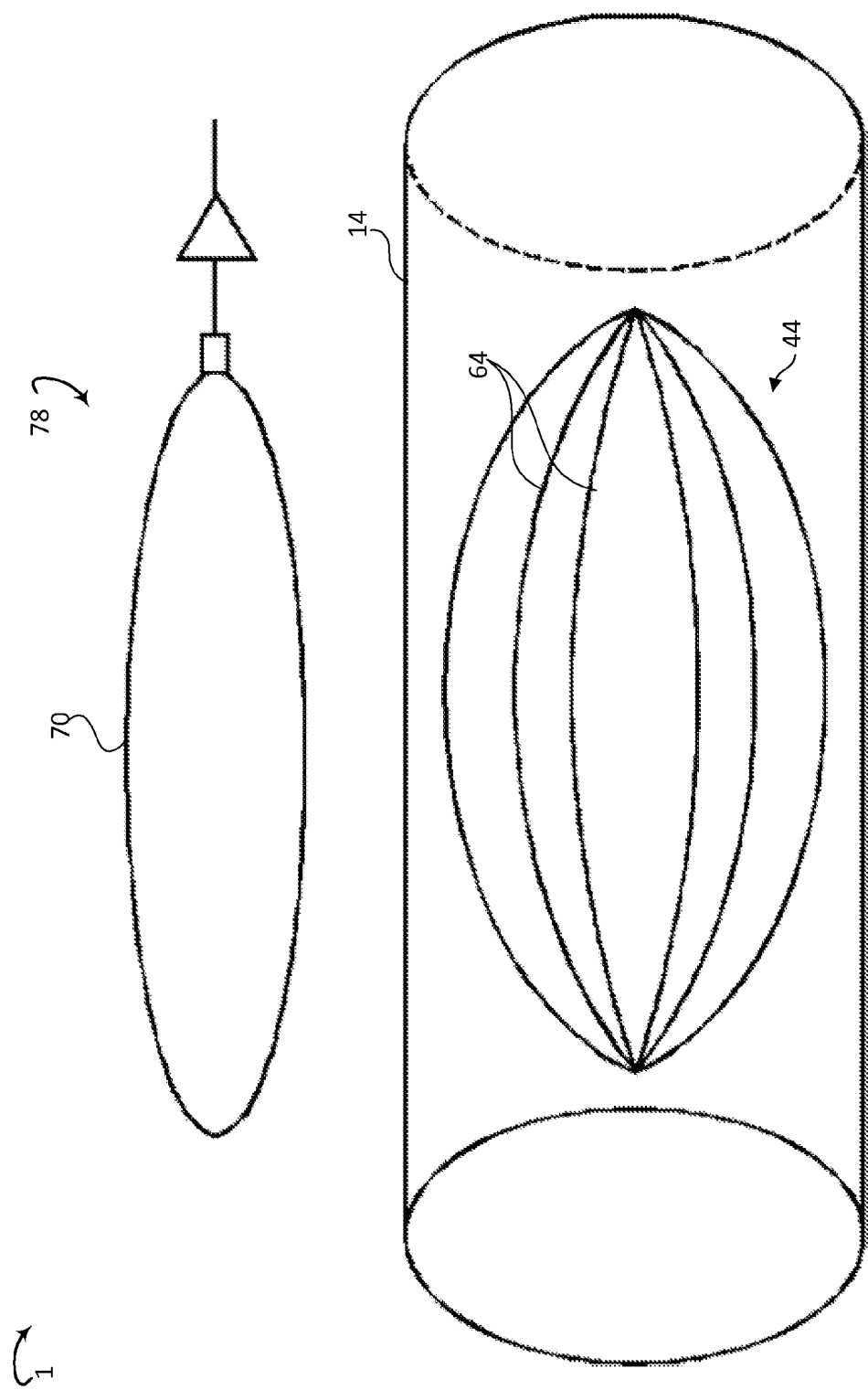

FIG. 10 diagrammatically illustrates one embodiment of the spreader with a surface coil.

Figure 11:
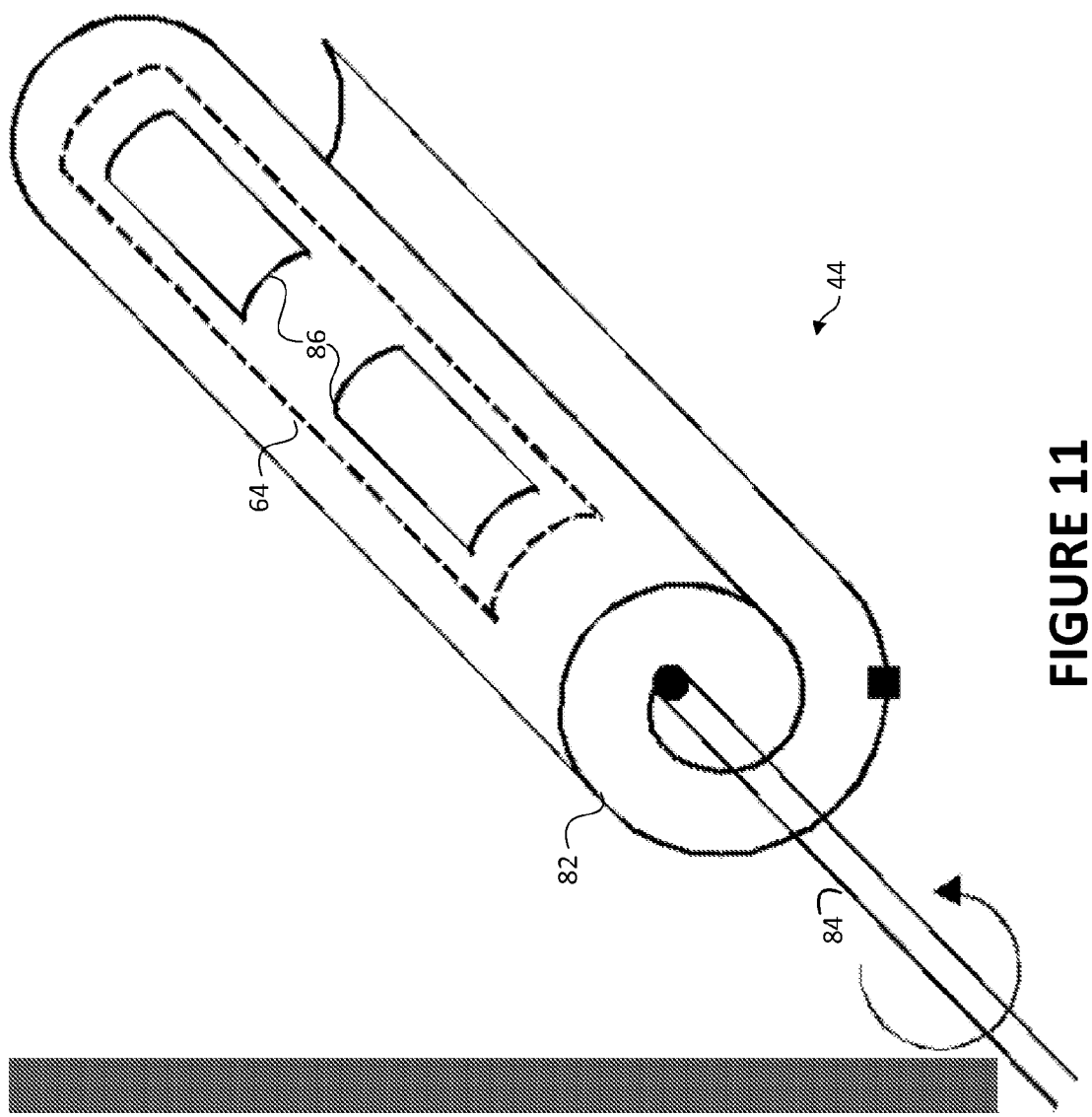

FIG. 11 diagrammatically illustrates one embodiment of a local prostate coil with a cylindrically shaped spreader.

FIGS. 12A and 12B illustrate embodiments of the relative distribution of the spreader and the coil elements.

Figure 13:
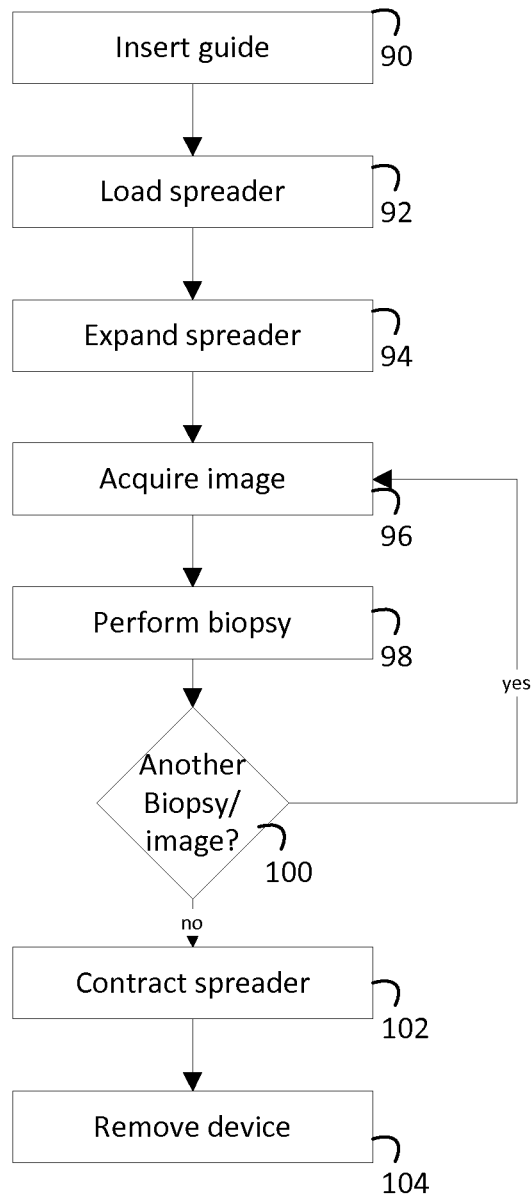

FIG. 13 flowcharts one method of using an embodiment of an local prostate coil with a spreader.

Figure 14:
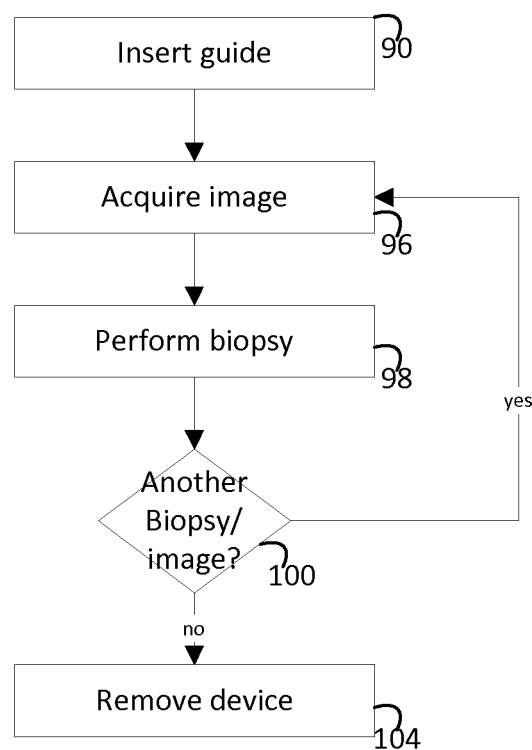

FIG. 14 flowcharts another method of using an embodiment of an endorectal prostate coil.

Figure 1:
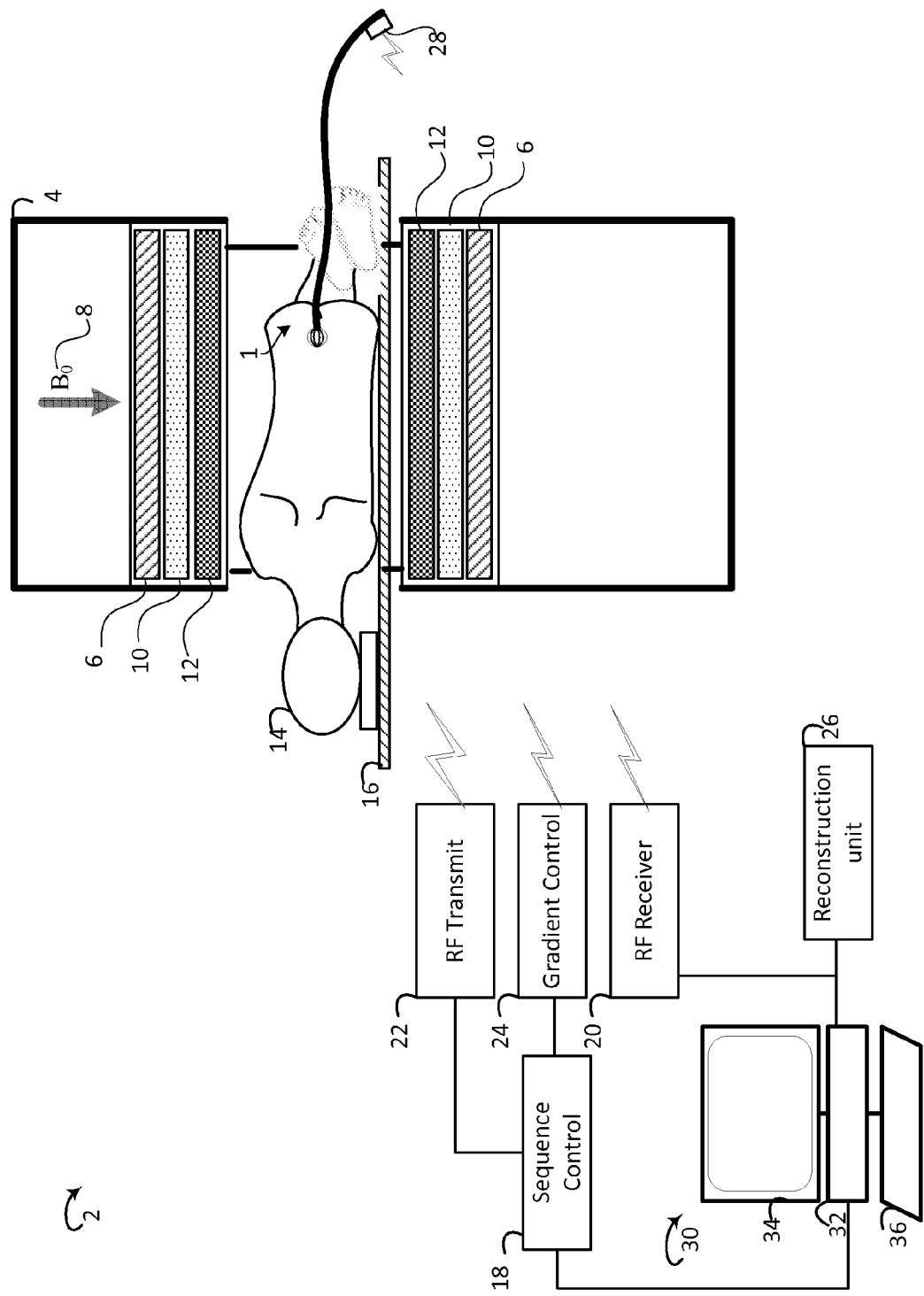

With reference to FIG. 1, one embodiment of an endorectal prostate coil 1 within a magnetic resonance (MR) system 2. The MR system 2 includes a MR scanner 4. The MR scanner 4 includes a main magnet 6 whose poles define the static main field ($B_0$) 8 such as a vertical main field. The MR scanner further includes one or more gradient coils 10 for applying gradient magnetic fields and one or more RF coils 12 which generate RF pulses to excite and manipulate magnetic resonance in a subject 14 and which, in some embodiments pick-up resonance signals from the subject. The MR scanner 4 includes an open design such as a panoramic or "C" type open scanner, but in other embodiments can include a horizontal bore. The subject is supported on a support 16 such as a horizontal bed or couch. The system includes a sequence controller 18 and a Radio Frequency (RF) receiver unit 20. The sequence controller 18 controls the operation of the imaging sequence implemented with a RF transmitter unit 22 controlling the operation of the RF coils 12 and a gradient controller 24 controlling the operation of the gradient coils 10. The communication between the controlling unit and the corresponding coils can be wireless, optical, or wired. The RF transmitter unit 22 works cooperatively with the local coil 1 when configured as a transmit/receive coil. The RF receiver 20 receives radio frequency or MR data from the local coil 1 indicative of the magnetic resonance excited in the tissue of the subject 14. The MR data can be communicated between the local coil and the RF receiver wirelessly, optically, or with a wired connection. With a wireless connection, power is used from an induced current or a separate power source to transmit MR data. With a wired connection, the wire can optionally supply power for amplification and other processing, and carry the resonance signal. A reconstruction unit 26, such as a processor, receives MR data from the RF receiver 20 and reconstructs one or more images from the received MR data.

The local endorectal coil 1 includes one or more electrically conductive elements tuned to receive orthogonal components of the induced magnetic resonance radio frequency signals which orthogonal components are orthogonal to the $B_0$ field, e.g. along the axis of the subject and transverse to the subject. The local coil can include an interface device 28 which communicates between the local coil and the RF receiver. The resonance signals inductively generate one or more currents indicative of the magnetic resonance. The one or more electrically conductive elements act as a local receive coil for tissue in the prostate region of the subject. When the local coil 1 is configured as a receive only local coil, the RF excitation and manipulation pulses is transmitted by the whole body RF coil 12. Optionally, with the power source and the controller can be used to control the one or more electrically conductive elements of the local coil to operate as a transmit and receive coil which both excites and/or manipulates magnetic resonance in the prostate tissue and receives the resonance signal.

The system 2 includes a workstation 30. The workstation 30 includes an electronic processor or electronic processing device 32, a display 34 which displays the images, menus, panels, and user controls, and the at least one input device 36 which inputs the healthcare practitioner selections. The workstation 30 can be a desktop computer, a laptop, a tablet, a mobile computing device, a smartphone, and the like. The input device can be a keyboard, a mouse, a microphone, and the like.

The various units or controllers 18, 24, 26 are suitably embodied by an electronic data processing device(s), such as the electronic processor or electronic processing device 32 of the workstation 30, or by a network-based server computer operatively connected with the workstation 30 by a network, or so forth. Moreover, the disclosed reconstruction and system operation are suitably implemented using a non-transitory storage medium storing instructions (e.g., software) readable by an electronic data processing device and executable by the electronic data processing device to perform the disclosed reconstruction and system operation.

The display 34 or display device as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Figure 2:
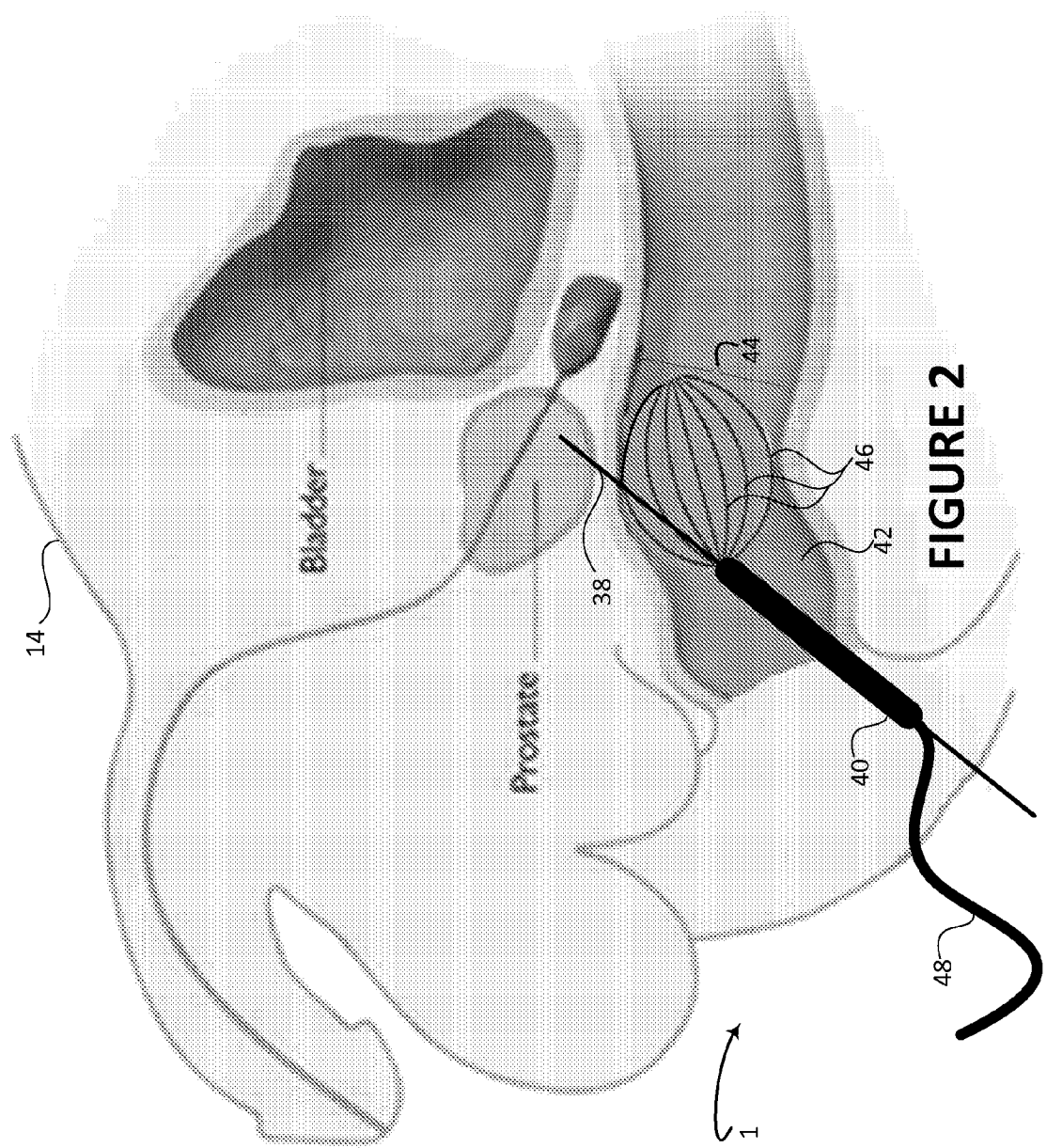

FIG. 2 diagrammatically illustrates one embodiment of the endorectal coil 1 with a deployed surgical instrument 38 such as a biopsy needle. The coil includes a guide tube 40 which is inserted into a rectum 42 of the subject. A spreader 44 is located at one end of the tube 40. The spreader 44 when unfolded or spread forms an elliptical shape. In another embodiment, the spreader is cylindrically shaped and uncoils with a twisting movement. Other shapes and selective expansion techniques are also contemplated. The spreader 44 includes a plurality of ribs or flexible supports 46 positioned at the end of the tube 40 and mechanically spread after the tube is inserted. The ribs 46 can include material such as rubber, polymers, non-ferrous metals, and the like which are spaced to provide open access for surgical instruments between the ribs such as inserting a needle to take a biopsy. The coil 1 can include one or more cables 48 such as a power cable for the coil, electrically conductive cable for transmitting the received magnetic resonance signals, a cable for controlling/spreading the spreader, and/or a cable for guiding/controlling surgical instruments. The cables extend from the other end of the tube.

The guide tube 40, the spreader 44, the surgical instruments 38, and/or the cables 48 can be made of a material which is inert or invisible to MR signals. Alternatively any one or a portion of any one of the tube, the spreader, the surgical instrument, or other items can be made of a material visible to MR signals. For example, a high quality stainless steel can be used to make the tube, the cables, and the surgical instruments invisible to MR. An MR visible coating can be applied to the surface of the tube and supports of the spreader such as a thin line to provide reference in the MR images as to the location of the tube, the needle, and/or the spreader. The coating can be a series of geometrical shapes such as lines with arrows to assist the healthcare practitioner in lining up the needle to take a biopsy sample. Geometric shapes such as bands around the tube, the needle, and or spreader can assist with distance measurement. In another example, instead of a coating, an MR visible material can be incorporated into the manufacturing of the tube, the instrument, and/or the spreader.

Figure 3:
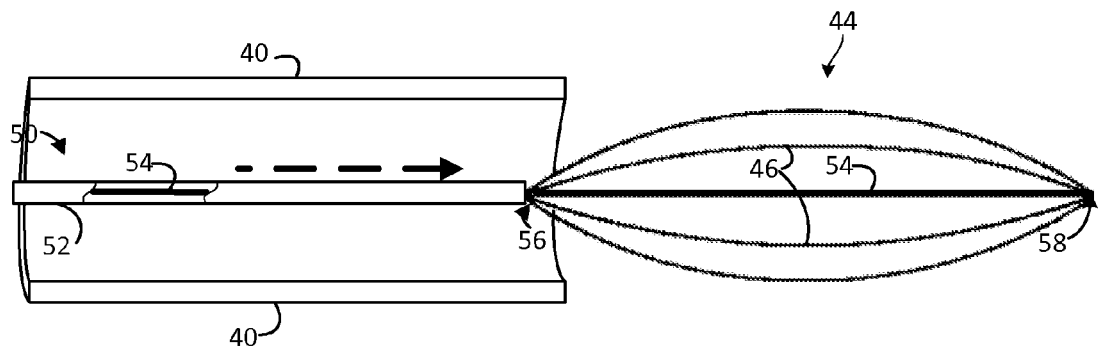
FIG. 3 illustrates one embodiment of the spreader deployment.

FIG. 3 illustrates one embodiment of the spreader 44 deployment through the tube 40. The spreader can be loaded through the tube in a collapsed state. Alternatively the spreader can be affixed to the tube prior to insertion in a collapsed state. Loading the spreader through the tube allows the material greater flexibility for the plurality of spaced ribs.

A cable, such as a Bowden cable 50, can be used to load the spreader into the proper position at the end of the tube after the tube insertion into the rectum. The Bowden cable 50 includes an outer cable 52 and an inner cable 54 which is shown in the cutaway view of the cable. In one configuration the outer cable 52 connects to the near end 56 of the spreader 44 and the inner cable 54 connects to the distal end 58 of the spreader 44. The cable pushes the spreader in the collapsed state through the tube and into the rectum.

Figure 4:
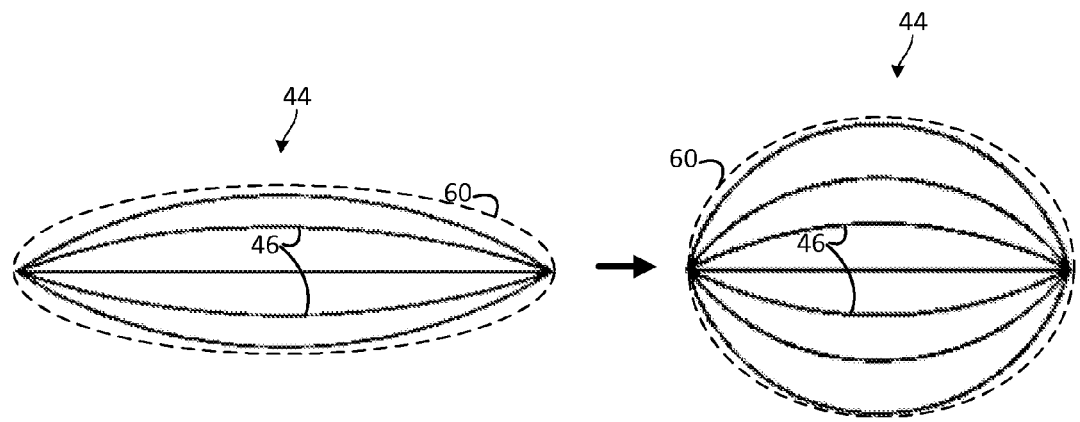
FIG. 4 illustrates one embodiment of the spreader being spread.

FIG. 4 illustrates one embodiment of the spreader 44 being spread. In a first image the spreader is in a folded or collapsed state. In a second image, the spreader is unfolded or expanded. The expansion can be controlled by a cable control such as a Bowden cable, swivel head screw, turnbuckle, etc. The size of the spreader is limited by the size of the rectum area when the spreader is unfolded or spread. In one embodiment, the spreader is sized to expand to stretch the rectum and flatten the prostate. For example, the inner cable 54 and the outer hollow cable or sheath 52 are used to urge a near end 54 and a distal end 56 of the spreader 44 closer together causing the ribs of the spreader to bend or arc further which makes the spreader shorter and wider, i.e. more nearly spherical. In another embodiment, the ribs 46 are resilient and pre-biased to the expanded configuration of FIG. 4. That is, the ribs are formed to adopt the expanded configuration in their relaxed state. The spreader is collapsed by insertion into the tube 40, by pushing the near and distal ends apart, pulling the rubs radially inward, or the like. For example, when the inner cable 54 of the Bowden cable is attached to the distal end and the hollow outer cable 52 is attached to the near end, advancing the inner cable into the hollow outer cable pushes the near and distal ends further apart. As another example, when the ribs 46 are in the collapsed configuration in the their relaxed state, withdrawing the inner cable 54 that is attached to the distal end 58 from the outer cable 52 that is attached to the near end 56 will pull the near and distal ends closer expanding the spreader 54. Other spreader constructions and mechanisms or other means for expanding or contracting the spreader are also contemplated.

In a spread or unfolded state, the spreader provides space between the flexible supports. The space between the flexible supports provides open access for surgical instruments to pass between the flexible supports to penetrate the walls of the rectum and prostate gland. The space created within the spread shape of the spreader provides maneuvering space to position the surgical instruments.

In one embodiment, the spreader is covered with a cover 60 such as a rubber, thin foil, etc. analogous to an umbrella. The cover material is selected such that it can be penetrated or pierced by surgical instruments. Piercing the cover does not collapse the spreader such as would occur with an inflated balloon or air supported structure. The cover acts as protection and allows for pushing back tissue.

FIG. 5 diagrammatically illustrates an embodiment of the guide tube 40 with the deployed surgical instrument 38, such as the biopsy needle. The tube carries a portion of the coil 1. The one or more cables can include the interventional device or surgical instrument 38 and a RF cable or a power supply cable. In the embodiment, the cable 48 such as the RF cable and/or the power supply cable can be integrated into the wall 62 of the tube 40.

With reference to FIG. 6, one embodiment of the local endorectal coil 1 with coil elements 64 located on the guide tube is diagrammatically illustrated. The local coil can include two electrically conductive loops 66 which can operate in quadrature when positioned with the x-axis generally parallel to the $B_0$ field. The electrically conductive loops can be wrapped around the guide tube 40. The electrically conductive loops are wrapped around the tube in a slanted pattern. The electrically conductive loops are wrapped to cross perpendicular to each other. Alternatively, the electrically conductive loops can be wrapped around a cable which passes through the tube. The electrically conductive loops operate in quadrature in a vertical main field when positioned generally horizontally with the x-axis generally vertically.

FIG. 7 diagrammatically illustrations another embodiment of the local endorectal coil 1 with coil elements 64 located on the guide tube 40. The coil elements 64 include one or more electrically conductive loops 66 formed on the surface of the tube in a saddle coil design 68. The saddle coil design operates in quadrature in a horizontal main field when positioned generally horizontally with the axis of the guide tube generally aligned with the $B_0$ field. Both embodiments described in FIGS. 6 and 7 can be realized as single element design as well as multichannel array designs, depending on the requirements for the intervention.

With reference to FIG. 8, one embodiment of the local endorectal coil 1 with coil elements 64 located on the spreader 44 is diagrammatically illustrated. The coil elements include two electrically conductive loops 70 shown with the spreader 44 in the unfolded or spread state. The two electrically conductive loops 70 are mounted on side surfaces of the spreader and generally orthogonal to each other to operate in quadrature. The two electrically conductive loops can be disposed on the surface of the optional cover 60 of the spreader or separately supported and integrated into the spreader. The individual electrically conductive loops shown with a tuning capacitor include a mechanical attachment to the spreader. As the spreader is spread, the conductive loops are also spread into a more nearly orthogonal relationship. The electrically conductive loops 70 include a preamplifier 72 and a matching and detuning circuit 74 such as PIN diodes.

Two or more of such coil elements described above may also be oriented alongside each other and possibly decoupled by overlap (as shown in FIG. 8). In such a design there would be no quadrature detection possible but the array character of the coil can be made use of e.g. by accelerating the imaging process using algorithms like SENSE or GRAPPA. The array layout may also be combined with the described design by placing, for example, 2 decoupled coil elements along the central axis of the spreader and another set of 2 decoupled elements rotated by 90°. The combination would result in an intrinsically decoupled 2 by 2 array coil.

With reference to FIG. 9, another embodiment of the local endorectal coil 1 with coil elements 64 integrated with the spreader 44 is illustrated. The ribs 76 include electrically elements that are configured to form a birdcage design. In one embodiment, capacitors are disposed in the electrically conductive elements to form a high-pass birdcage coil. Positioning capacitors in the end rings to form low-pass or band pass birdcage coils are also contemplated. Distributing the capacitors over the conductive loops reduces local high electrical fields. Another design contemplates the capacitors located in loop coils formed using electrically conductive material integrated with opposite ribs or adjacent ribs. In another embodiment, the conductive elements 64 are disposed on the covering material 60. The local coil 1 can be designed as a receive only coil or a transmit and receive (T/R) coil.

The local coil can include a tuning and matching circuit 74. PIN diodes can be used to detune the local coil 1 during transmit. The tuning and matching circuit 74 matches the coil impedance to the noise impedance of the preamplifier. The tuning and matching circuit 74 matches the resonant structure to the preamplifier or transmitter and adjusts the tuning and matching to compensate for the change in coil impedance with the spreading of the spreader 44 and corresponding change in coil configuration, particularly a diameter. If the matching range is exceeded image degradation can result. In one embodiment, a sensor, such as a local reflectormeter and a processor, transmits a signal to the tuning and matching circuit 74 and/or the system 2 such as the processor of the workstation 30.

With reference to FIG. 10 one embodiment of the spreader with a surface coil 78 is illustrated. The spreader 44 includes one or more electrically conductive coil elements 64 which form a wireless resonant coil with diodes (not shown) for passive detuning The coil elements 64 of the spreader 44 are inductively coupled to the external surface coil 78 located on the body surface. With the inductively coupled surface coil 78 and the wireless resonant coil formed by the electrically conductive elements 64 of the spreader 44, a higher signal to noise ratio (SNR) can be obtained.

FIG. 11 illustrates one embodiment of the local endorectal coil 1 in which the spreader 44 is cylindrically shaped. In one embodiment, the spreader includes a rolled strip of material 82. The material can be resilient to form a roll spring. The spreader 44 can change diameter by rotation of the center edge of the strip relative to the peripheral edge. By rotating a stub 84 attached to the center edge, the diameter can be increased and/or decreased. The spreader 44 includes cut-outs 86 which provide open access for surgical instruments. In one example, the cut-outs can span most of the width and have only thin structured dividers between them. The edges and structural dividers can carry a birdcage coil, loop coil, TEM coils, etc. The spreader 44 includes or carries one or more electrically conductive elements 64 which are located on a surface of the spreader, i.e. on the strip of material 82. In another embodiment, the one or more elec-trically conductive elements 64 are located on the stub 84 such as the coil configurations of FIGS. 6 and 7.

FIGS. 12A and 12B illustrate embodiments of the relative distribution of the spreader and the coil elements. The spreader and/or coil elements such as the one or more conductive loops are preferably disposable. With reference to FIG. 12A, the one or more conductive elements 64 are disposed on the surface of the spreader 44 such as a metallic coating. With reference to FIG. 12B, the one or more conductive elements 64 can be integrated into the spreader 44 such as embedding an electrically conductive material such as a wire or foil within the ribs.

FIG. 13 flowcharts one method of using an embodiment of the local prostate coil with a spreader. In a step 90 the tube 40 is inserted into the rectum of the subject. The tube can include MR visible material or be invisible. Once the tube is positioned in the rectum, the spreader 44 is loaded in a step 92 through the tube 40 and positioned at the end of the tube within the rectum. In a step 94, the spreader is unfolded or expanded. The spreader can be expanded using a control cable such as a Bowden cable, a stub, swivel screw or the like.

MR data is acquired in a step 96 and one or more images reconstructed by the MR system. In one embodiment, the MR data is acquired with the electrically conductive elements 64 disposed on the spreader 44 or the cover 60. In another embodiment, the MR data is acquired with one or more electrically conductive elements 64 disposed about the guide tube 40. In another embodiment, the one or more electrically conductive elements 64 are disposed on the end of a cable or on the stub 84 which is inserted through the guide tube 40. In another embodiment, MR data is acquired using the surface coil 78 inductively coupled with passive coil elements 64 disposed in the spreader 44. In yet another embodiment a surface coil or a surface coil array can be utilized to aquire images in combination with the coils on the device described above or without using the internal coils. The images of the surface coil may serve as a survey type set of images for coarse orientation while the coils of the device are likely used for imaging the rather small field of view of interest, once the device is positioned correctly.

In a step 98, the tube is positioned by the healthcare practitioner based on the one or more reconstructed images. A surgical instrument, such as a biopsy needle, is inserted through the tube and into the target in the prostate under the guidance of the repeatedly acquired images, and the biopsy sample is taken. For example, the healthcare practitioner positions the tube to direct the biopsy needle in between the ribs 46 or through the cutouts 86 of the spreader through the rectum and into the prostate. In the embodiment of the spreader with the cover 60, the needle penetrates the cover to take the biopsy sample.

In a decision step 100, the healthcare practitioner can repeat the imaging and positioning of the guide and/or surgical instrument to take additional biopsy samples. The order of positioning and imaging can be simultaneous as the system is acquiring MR data and reconstructing ciné images while the healthcare practitioner positions the tube and/or intervention device and/or surgical instruments. The healthcare practitioner undertakes the biopsy separate from the MR data acquisition and image reconstruction.

The spreader is folded, contracted, or collapsed in a step 102. The collapsing of the spreader is performed by the healthcare practitioner using the control cable, stub, etc. The spreader can be withdrawn through the tube or remain attached to the tube as the tube is removed in a step 104.

FIG. 14 flowcharts another method of using an embodiment of an endorectal coil 1. In a step 90, the tube is inserted into the rectum by the healthcare practitioner. The tube or a separate cable fitted with one or more electrically conductive loops acquire the magnetic resonance signals in a step 96. The magnetic resonance signals are reconstructed into one or more images. In a step 98, the tube is positioned and an intervention, such as a biopsy, is performed using the surgical instruments and/or interventional device. The steps of acquiring additional images and performing a biopsy can be repeated based on a decision step 100. After the biopsy or intervention is finished, the local prostate coil which includes the tube is removed in a step 104.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An endorectal coil comprising:
a tube configured for insertion into a rectum;
a spreader including a plurality of ribs configured to pass through the tube in a collapsed configuration and be positioned at a distal end of the tube and configured to be mechanically spread after emergence from the tube to compress surrounding tissue after the tube is inserted, when spread, the ribs defining openings therebetween configured to pass a surgical instrument, wherein the plurality of ribs are connected together at a near end and a distal end of the spreader;
one or more coil elements tuned to receive magnetic resonance data, the coil elements being carried by the spreader, and configured to be pressed against walls of the rectum by the spreader; and
a cover which covers the spreader and expands with the spreader to provide a surface that is mechanically penetrable by surgical instruments without collapsing.

2. The endorectal coil according to claim 1, wherein the one or more coil elements include loop coils that are at least one of:
attached to the spreader; and
attached to the cover of the spreader; and
wherein the loop coils are configured to move into an orthogonal relationship as the spreader spreads.

3. An endorectal coil comprising:
a tube configured for insertion into a rectum;
two conductive loops wrapped around the tube in a slanted criss-cross pattern such that when the tube is disposed generally horizontally in a vertical main field, the conductive elements receive in quadrature;
a spreader including a plurality of ribs configured to pass through the tube in a collapsed configuration and be positioned at a distal end of the tube and configured to be mechanically spread after emergence from the tube to compress surrounding tissue after the tube is inserted, when spread, the ribs defining openings therebetween configured to pass a surgical instrument; and
one or more coil elements tuned to receive magnetic resonance data, the coil elements being carried by the spreader, and configured to be pressed against walls of the rectum by the spreader.

4. A method of imaging with an endorectal coil, comprising:
inserting a tube through the rectum;
compressing tissue surrounding the tube including mechanically spreading a spreader positioned at the end of the tube wherein the spreader includes a coiled strip of material and wherein the step of spreading the spreader includes uncoiling the coiled strip of material, the coiled strip defining the plurality of openings configured to pass a surgical instrument therethrough;
after spreading the spreader, inserting the surgical instrument through the tube and one of a plurality of openings in the spreader;
acquiring magnetic resonance data by an RF coil supported on the coiled strip; and
reconstructing the magnetic resonance data into images.

* * * * *